United States Patent

Kriz et al.

[11] Patent Number: 6,110,660
[45] Date of Patent: *Aug. 29, 2000

[54] PROCEDURE FOR QUANTITATIVE AND QUALITATIVE DETERMINATION OF CHEMICAL SUBSTANCES, BASED ON MOLECULAR RECOGNITION AND MEASUREMENT OF MAGNETIC PERMEABILITY

[75] Inventors: Dario Kriz, Malmö; Karin Marie Christine Berggren, Lund, both of Sweden

[73] Assignee: The European Institute of Science AB, Lund, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/847,125

[22] Filed: May 1, 1997

[51] Int. Cl.[7] .............................. C12Q 1/00; C12Q 1/70; C12Q 1/68; G01N 33/53

[52] U.S. Cl. .................. 435/4; 435/5; 435/6; 435/7.1; 435/7.2; 436/501; 422/50; 422/68.1; 422/69; 422/82.01

[58] Field of Search .................. 435/5, 7.1, 7.2, 435/4, 6; 422/50, 68.1, 69, 82.01; 436/501; 935/77, 78

[56] References Cited

U.S. PATENT DOCUMENTS

| | | | |
|---|---|---|---|
| 4,219,335 | 8/1980 | Ebersole | 23/230 B |
| 5,200,270 | 4/1993 | Ishida et al. | 428/403 |
| 5,260,050 | 11/1993 | Ranney | 424/9 |
| 5,270,644 | 12/1993 | Rhoads et al. | 324/204 |
| 5,653,939 | 8/1997 | Hollis et al. | 422/50 |

OTHER PUBLICATIONS

C.W. Babb, et al., *Analytical Chemistry* 67(4):763–769 (1995).
J. Janata, *Journal of the American Chemical Society* 97(10):2914–2916 (1975).
J. Janata, et al., *Analytical Chemistry* 66(12):207R–228R (1994).
C.B. Kriz, et al., "Magnetic Permeability Measurements in Bioanalysis and Biosensors," *Analytical Chemistry* 68(11):1966–1970 (1996).
D. Kriz, "Towards Chemical Sensors Based On Conducting And Molecularly Imprinted Polymers," Lund, Sweden (1994).
J.S. Schultz, et al., *Biotechnology Bioengineering Symp.* 9:65–71 (1979).
P. Wikström, et al., *Analytical Biochemistry* 167:331–339 (1987).

*Primary Examiner*—Ardin H. Marschel
*Attorney, Agent, or Firm*—Knobbe, Martens, Olson & Bear, LLP

[57] ABSTRACT

A system for very sensitive detection and/or quantification of an analyte is disclosed. The system is based on an interaction, such as specific binding or competitive displacement from a ligand, between an analyte and a ferromagnetic marker. The great difference in magnetic permeability between the ferromagnetic marker and the background allows detection of very small quantities of analyte, based on the marker's induction of a changed magnetic permeability for the sample being measured.

58 Claims, 6 Drawing Sheets

PROCEDURE FOR QUANTITATIVE AND QUALITATIVE DETERMINATION OF CHEMICAL SUBSTANCES, BASED ON MOLECULAR RECOGNITION AND MEASUREMENT OF MAGNETIC PERMEABILITY

FIELD OF THE INVENTION

This invention relates to quantitative and qualitative determination of chemical substances (analytes) based on sensitive measurements of magnetic permeability.

BACKGROUND OF THE INVENTION

Research on biosensor technology has, during the last two decades, been very intensive, as shown by the numerous publications and patent applications submitted worldwide. See, e.g., Janata, J., Jasowicz, M., and DeVaney, D. M., (1994) *Anal. Chem.* 66:207R–228R. The reasons for these efforts are the potential advantages that such techniques offer compared to alternative, already established, analytical procedures, such as high performance liquid chromatography, bioanalytical procedures such as radio- or enzyme labeled immunoassays, and spectrophotometric bioassays. The advantages of biosensor technology include simplicity and rapidity, reduction of the need for sample pre-treatment, the low cost of the analytical equipment, avoidance of the use of hazardous chemicals, the wide range of analytes which may be measured, and excellent selectivity and sensitivity. However, affinity biosensors have shown generally poor results, since the operational principle involves only a binding reaction between the analyte and the recognition element in the biosensor. Thus, no analyte conversion occurs. This makes it necessary to use various labeling techniques or to use mass-change sensitive transducers such as potentiometric, optical and piezoelectric transducers. Turner, A. P. F. (1994) *Curr. Opin. Biotechnol.* 5:49–53. Instruments of this type are often very sensitive to non-specific interactions with the matrix.

Magnetism has been used for specific isolation on an industrial scale. An example is the so called HGMS-technique (High Gradient Magnetic Separator), which is used in large-scale processes such as water purification, treatment of kaolin, and cell/protein isolation with magnetic particles. Also available commercially are inductive sensors that are based on the principle that a coil measures a change in the magnetic field. These inductive sensors react on physical means such that, for example, a magnet or a ferromagnetic material is connected to a float in a tank, with the inductive sensor responding to the level of the solution in the tank.

Several current techniques include measurements of magnetic fields or magnetic permeability for the determination of the content of magnetic material in a sample. Examples of magnetic materials whose presence in samples may be thus detected are: magnetite in ironstone, iron oxide in slag, catalytically active nickel in the process for hydrogenation of fat, iron in oils, and ferromagnetic materials in cement mixtures. Measurements of magnetic fields or magnetic permeability are also used in detection of paramagnetic ions, control of hardmetal alloys, and in magnetic oxygen analyzers. These determinations are not based on molecular recognition, and therefore they often provide a low specificity. These methods are also limited by the fact that they can detect and/or quantify only ferromagnetic materials, and are not adapted to detection of nonmagnetic materials.

Magnetically active reagent carriers as disclosed in U.S. Pat. No. 5,200,270 are useful for the transportation of antibodies, enzymes and haptens in, for example, immunoassays. The '270 patent only describes the use of the carrier for isolation or cleanup, while it is suggested that this can be combined with other chemical analysis techniques. The measurement of magnetic permeability on the carrier particles themselves is not mentioned. The same is true of Japanese patent application JP 62118255 A, which discloses the use of magnetic particles in a similar way for chemical analyses, where the measurement is based on light scatter phenomena.

Measurement of changes in a magnetic field have been reported, such as in combination with oxygen-consuming magnetotactic bacteria, for prediction of aquatic hypoxia, as disclosed in U.S. Pat. No. 5,270,644. This patent describes measurements of magnetic fields on layers of bacteria containing magnetic particles. The abundance of these bacteria in such layers contributes to the strength of the magnetic field, and correlates negatively with the oxygen content in the surrounding environment.

Biomagnetic neurosensors have also been reported. Babb, C. W., Coon, D. R., and Rechnitz, G. A., (1995) *Anal. Chem.* 67:763–769. This work is based on measurements of magnetic fields that arise from movements of ions in a nerve. Such movements create an electrical current and give rise to an induced magnetic field. This type of magnetic measurement, however, is not based on measurement of a material constant. These kinds of measurements of magnetic fields may be distorted by the great amount of electronic noise in many ambient settings. Furthermore, only substances which can affect the bacteria or nerve, in these examples, can be detected, and the complex response can be very difficult to interpret.

Relative magnetic permeability, $\mu_r$, is a material constant. This material constant constitutes a measure of a substance's ability to contain and contribute to an externally applied magnetic field. As examples of substances that are classed as ferromagnetic materials ($\mu_r \gg 1$), the transition elements and phases of the following elements are included: iron, nickel, cobalt, gadolinium and manganese, as well as chemical compounds, semiconductors, or alloys containing these elements. The relative magnetic permeability for practically all other materials is about 1. See Table 1 and Djurle, E., (1983) Electricitetslära, Teknisk Högskolelitteratur i Stockholm AB, Sweden. The relationship between magnetic permeability ($\mu$) and relative magnetic permeability ($\mu_r$) can be described according to the following formula:

$$\mu = \mu_r \times \mu_0, \text{ where } \mu_0 \text{ is a constant with a value of } 4\pi \times 10^{-7} \text{ H/m}.$$

TABLE 1

| Substance | Material constant $\mu_r$ |
|---|---|
| Lead | 0.999983 |
| Copper | 0.999990 |
| Water | 0.999910 |
| Platinum | 1.000293 |
| Aluminum | 1.000021 |
| Air | 1.00000036 |
| Iron | 600–1,000,000 |

The specific chemical detection or quantification of a substance demands the presence of a recognition element which recognizes the analyte. Kriz, D., (1994) Towards chemical sensors, Lund, Sweden. Molecular recognition between the recognition element and the analyte can be based on many different types of interactions, such as electrostatic, hydrophobic, hydrogen bonds and van der Waals forces. After the initial recognition step, the chemical event is transformed to a physically measurable signal based on, for example, electrochemical, mass, optical, and/or thermometrical properties. In contrast, the present invention is based on changes in magnetic permeability for detection or quantification of a substance. These changes can be correlated to the amount of analyte in the measurement solution, providing a new and advantageous mode of chemical detection and quantification.

SUMMARY OF THE INVENTION

The present invention provides a system for detection of an analyte. The system of the invention includes a marker, a recognition element, and a transducer, the marker including a material having a relative magnetic permeability constant of at least about 600, the recognition element being capable of binding to or competing for binding with the analyte, and the transducer being adapted to be induced proportional to the magnetic permeability of a sample. The marker and the recognition element act to induce in the transducer a first inductance value when the analyte is absent from the sample, and a second inductance value when the analyte is present in the sample.

In this aspect of the invention, the marker may specifically bind to the analyte. Alternatively, the marker may compete with the analyte for binding to the recognition element. In another embodiment of this aspect of the invention, the recognition element may be linked to the marker, or the recognition element and the marker may both bind to the analyte.

This aspect of the invention contemplates numerous possible analytes, including but not limited to: a ferromagnetic marker, a protein, a nucleic acid, a hormone, an antibody, a virus, a cell, and the like. In this aspect of the invention, the second inductance value may be quantitatively proportional to the concentration of the analyte in the sample. The proportionality may be inverse or direct, depending on the type of measurement performed. The sample may be a soluble solution or a suspension, including, for example, a centrifugation supernatant. Alternatively, the sample may be or include a particulate fraction, including, for example, one or more of the following particulate components: a centrifugation pellet, cells, viruses, beads, and the like.

The marker material of this aspect of the invention may contain one or more elements selected from the group consisting of iron, nickel, cobalt, gadolinium and manganese. The material may be, for example, an alloy, a semiconductor, a chemical compound, and the like. The transducer may be a coil adapted to accept inductance proportional to the magnetic permeability of the sample, and may include an electronic measuring bridge. An example of such a bridge is a Maxwell bridge. In another embodiment, the transducer may be an LC-circuit.

A second aspect of the invention provides a method of detecting an analyte. A first step of the method is to provide a sample that includes a marker and a recognition element, the marker being a material having a relative magnetic permeability constant of at least about 600, and the recognition element being capable of binding to or competing for binding with the analyte. The marker and the recognition element of this aspect of the invention are adapted to cooperate to induce in a transducer a first inductance value when the analyte is absent from the sample, and a second inductance value when the analyte is present in the sample. Additional steps of the method of this aspect of the invention include inducing an inductance value in the transducer by positioning the sample in the vicinity of the transducer, and determining whether the analyte is absent or present in the sample, based on the inductance value induced in the inducing step.

In this aspect of the invention, the marker may specifically bind to the analyte. Alternatively, the marker may compete with the analyte for binding to the recognition element. In another embodiment of this aspect of the invention, the recognition element may be linked to the marker, or the recognition element and the marker may both bind to the analyte.

This aspect of the invention contemplates numerous possible analytes, including but not limited to: a ferromagnetic marker, a protein, a nucleic acid, a hormone, an antibody, a virus, a cell, and the like. In this aspect of the invention, the second inductance value may be quantitatively proportional to the concentration of the analyte in the sample. The proportionality may be inverse or direct, depending on the type of measurement performed. The sample may be a soluble solution or a suspension, including, for example, a centrifugation supernatant. Alternatively, the sample may be or include a particulate fraction, including, for example, one or more of the following particulate components: a centrifugation pellet, cells, viruses, beads, and the like.

The marker material of this aspect of the invention may contain one or more elements selected from the group consisting of iron, nickel, cobalt, gadolinium and manganese. The material may be, for example, an alloy, a semiconductor, a chemical compound, and the like. The transducer may be a coil adapted to accept inductance proportional to the magnetic permeability of the sample, and may include an electronic measuring bridge. An example of such a bridge is a Maxwell bridge. In another embodiment, the transducer may be an LC-circuit. In the method of this aspect of the invention, positioning the sample may include flowing the sample through the vicinity of the transducer.

A third aspect of the present invention provides a method for detecting the presence of an analyte. One step of this method is to contact a sample suspected of containing the analyte with a reagent that binds to or competes for binding with or by the analyte. The reagent includes a component having a relative magnetic permeability constant of at least about 600. Additional steps of this aspect of the invention are separating unbound reagent from bound reagent, and detecting or measuring the bound or unbound reagent as an indication of the presence, absence, or quantity of the analyte in the sample.

BRIEF DESCRIPTION OF THE DRAWINGS

FIGS. 1a–1c depict schematically three different approaches to analyte detection, based on the combination of molecular recognition and measurement of the magnetic permeability.

DETAILED DESCRIPTION OF THE PREFERRED EMBODIMENT

Parallel to the development of biosensors, the potential of biomagnetic separation techniques has been increasingly recognized, mostly because of the efficiency, simplicity, mild operating conditions, and low cost of the techniques. The present invention extends the use of magnetic phenomena into biosensor and bioassay technology. The novel type of magnetic transducers disclosed herein, when used in combination with ferromagnetic labels, exhibit very low interference from the sample matrix, as they are only sensitive to ferromagnetic substances, which rarely are present in most biological samples. In addition, no fouling of the transducer occurs. Earlier work in this area included measurements of induced currents caused by ion migration in nerves. The drawbacks of these earlier efforts include the non-general nature of the approach, the complex response signal due to the huge number of substances that stimulate the nerve, and interference from electronic noise in the surroundings.

Materials having a very high $\mu_r$ are known as ferromagnetic materials. Examples of ferromagnetic materials are the elements iron, nickel, cobalt, gadolinium and manganese. In addition to the foregoing elements, ferromagnetic phases, chemical compounds, alloys and semiconductors also exist and can be adapted for use in the present invention.

We disclose herein the feasibility of using magnetic permeability measurements in bioanalysis-biosensors. This approach is also useful for the investigation of other recognition element-analyte systems (antibodies/antigens, receptors/peptides), targeted covalent binding, or DNA/DNA hybridization studies. The data obtained can be used to indicate the presence of an analyte and to calculate its concentration.

The main advantages of detection using magnetic permeability measurements are the simplicity compared with classical immuno-analysis methods, the possibility of real time monitoring of the recognition element-analyte complex formation, the low or non-existent interference from the sample and the fact that hazardous radio labels or unstable enzyme labels are not required.

With the sensitivity of detection as disclosed herein, it is possible to detect picomolar concentrations of macromolecules such as proteins, hormones, antibodies, and the like. It is also possible to detect microbes or viruses at very low concentrations, such as a an early stage of infection.

Figure 1A:
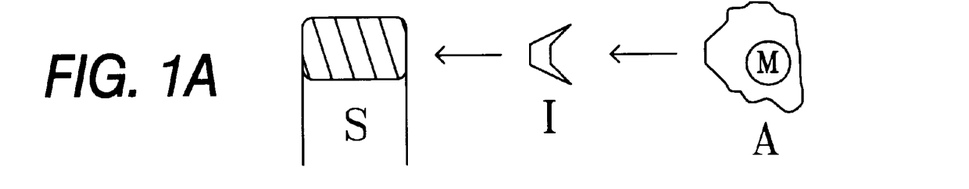
FIG. 1a shows the direct detection of a ferromagnetic analyte.
Figure 1B:
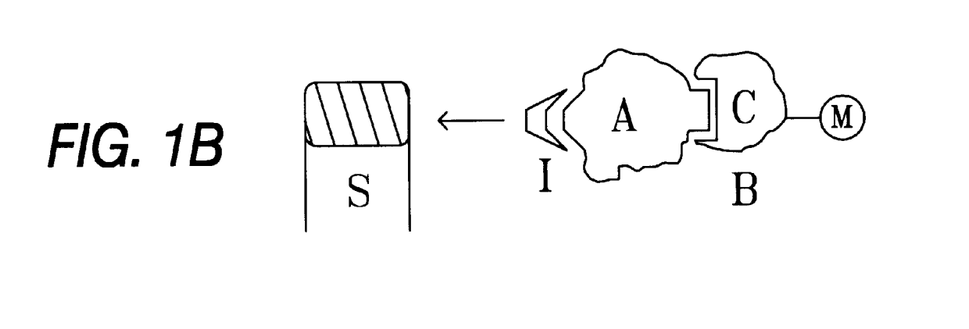
FIG. 1b shows an analyte specifically bound by a ferromagnetically-labeled ligand.
Figure 1C:
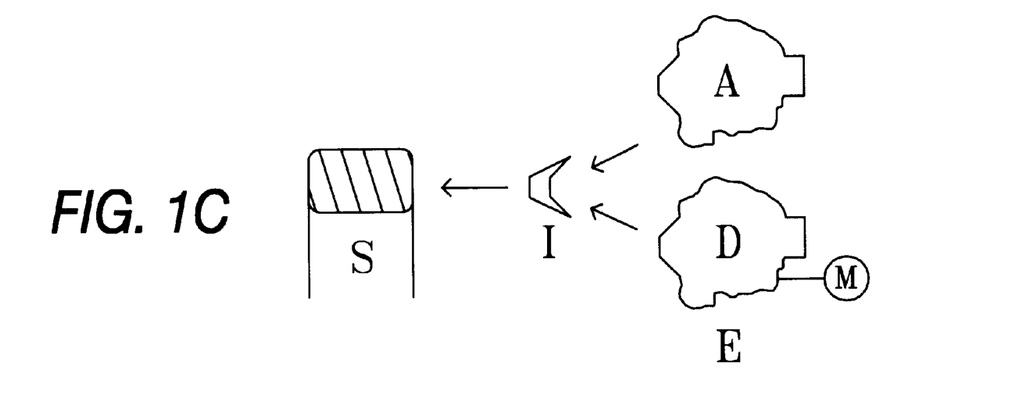
FIG. 1c represents competitive detection using a labeled competitive analogue of the analyte.

Three main approaches for bioanalysis, based on the principle of detecting changes in the magnetic permeability, are disclosed herein, as shown in FIG. 1:

First, analysis can be performed directly on certain analytes (A), which themselves have high enough magnetic permeability ($\mu_r \gg 1$) to give a measurable local change of the material constant ($\mu_r$) arising from the formation of a complex between the analyte (A) and the recognition element (I) and which can be detected with a coil (S). Analytes detectable in this way contain a ferromagnetic material (M). See FIG. 1a and FIG. 2.

Second, analysis can be performed on other analytes (A), which have low magnetic permeability ($\mu_r \approx 1$), where an analyte binding marker (B) having a high magnetic permeability ($\mu_r \gg 1$) is allowed to bind to the analyte, either before or after the binding of analyte to the recognition element (I). The sequential or "sandwich" binding of analyte to recognition element and marker to analyte, induces a measurable local change in the material constant ($\mu_r$). The analyte binding marker (B) contains both a ferromagnetic material (M) and a binding substance (C) which is directed against another epitope on the analyte than the one that the recognition element is directed against. See FIG. 1b.

Third, analysis can be performed on analytes (A), which have a low magnetic permeability ($\mu_r \approx 1$) whereby an analyte-resembling marker (E) with high enough magnetic permeability ($\mu_r \gg 1$) is allowed to bind the recognition element (I) in a competitive manner with the analyte (A). The competitive binding induces a measurable local change in the material constant ($\mu_r$) proportional to the formation of a complex (A-I or B-I) between the analyte (A) or the marker (B) and the recognition element (I). The analyte-resembling marker (B) contains both a ferromagnetic material (M) and a substance (D) which are the analyte (A) or a analyte-resembling substance which can compete for the binding to the recognition element (I). In this example, the presence and concentration of the analyte may be determined by the lowering of the magnetic permeability in the sample, arising from displacement of the ferromagnetic competitive marker by the non-ferromagnetic analyte. See FIG. 1c and FIG. 3.

The magnetic permeability for the material inside or in the vicinity of a coil or a conductor affects its inductance. This makes it possible for inductive measurements to determine the magnetic permeability, which leads to the quantification of the analyte. This can be done directly by measurement of the magnetic permeability on the recognition element, which may also include the matrix on which it is immobilized. A more indirect way is to measure the decrease in magnetic permeability in the measuring solution based on competition between the analyte and a ferromagnetic marker having similar affinity for the molecular recognition element.

The magnetic permeability of a material inside a coil influences the inductance of the coil. It is thereby possible to detect changes in magnetic permeability using inductance measurements. As an example, the inductance for a long coil is described by equation 1:

$$L = (\mu_r \mu_0 A/l) N^2 \text{ (generally inside the coil)} \qquad (1)$$

where $\mu_r$ represents the relative magnetic permeability of the material in the coil, $\mu_0 = 4\pi \times 10^{-7}$ Vs/Am, and represents the permeability of a vacuum, A is the cross sectional area, l is the length of the coil and N is the number of turns in the coil. To measure the inductance, and thus indirectly the relative magnetic permeability, the coil can be placed in a Maxwell bridge.

If A, l and N are kept constant, and if a controlled amount of material is inside the coil, the magnetic permeability of the material can be determined. The inductance can be measured in several different ways, such as, for example: by placing the coil in an electrical measuring bridge, such as, for example, a Maxwell bridge; by measurement of the resonance frequency for an LC-circuit of which the coil is a part; by applying a potential pulse and measuring the current response; by applying a current pulse or a non-constant current (where the current change per time di/dt is kept constant), while monitoring the potential response; by inductive coupling between two coils; and by measurement of the coil's impedance. Djurle, E., (1983) *Electricitetslära*, Teknisk Högskolelitteratur i Stockholm AB, Sweden; and Grahm, L., Jubrink, J.-G., and Lauber, A. (1992) Elektrisk m äitteknik 1&2, Bokförlaget teknikinformation, Lund and Linköping, Sweden.

The present invention is therefore a new magnetic transducer for bioanalysis and biosensors, based on the measurement of magnetic permeability. As a model system, and not by way of limitation, Concanavalin A (Con A) was chosen as the biorecognition element for a magnetic affinity biosensing device. Con A has been used previously as the recognition element in potentiometric affinity biosensors. Janata, J., (1975) *J. Am. Chem. Soc.* 97:2914–2916. It belongs to the family of lectins and is frequently used as a model system due to its high affinity for various sugars, such as glucose and dextran. The interactions of Con A with glucose and dextran have been used in an optical transducer-based competitive assay. Schultz, J. S., and Sims, G., (1979) *Biotechnol. Bioeng. Symp.* 9:65–71. This disclosure demonstrates the new magnetic transducer principle in both the direct detection mode and the competitive mode. A ferromagnetic dextran ferrofluid was used as an analyte in the direct mode, and in the competitive mode the same dextran ferrofluid was used as a ferromagnetic competitor with a non-ferromagnetic analyte, glucose.

Although specific procedures are illustrated, it will be understood that a large number of specific or targeted binding interactions are known in the prior art, as are techniques for linking labels, such as ferromagnetic moieties, to specific binding partners. These interactions are so well known and exist in such variety that a person of ordinary skill in the art can apply the present invention to any particular desired interaction system without undue experimentation. One aspect of the invention is not limited to any particular interaction; rather, it is intended to be applicable to and to encompass the entire field of applicable binding interactions, since the invention resides in the use and detection of ferromagnetic moieties, and not only in the binding interaction itself.

EXAMPLES

Example 1. Chemicals, Procedure, and Measurements

Chemicals

Con A Sepharose CL-4B and Sepharose CL-4B were purchased from Pharmacia Biotech (Sweden). Dextran ferrofluid was manufactured according to previously described procedures. Wikström, P., Flygare, S., Gröndalen, A., and Larsson, P.-O., (1987) *Anal. Biochem.* 167:331–339. The iron content was determined by atomic absorbance measurements to be 10 mg/ml, and the dry weight content was 78 mg/ml. The size distribution of the particles in the dextran ferrofluid was examined by gel chromatography and was found to be heterogeneous, in the range of 20–200 nm. All other chemicals used were of analytical grade.

Binding procedure

Before use, the Con A Sepharose gel was washed 10 times with 5 ml binding buffer (0.02 M Tris-(hydroxymethyl)-aminomethane—hydrochloric acid, pH 7.4 and 0.5 M sodium chloride) to remove the storage buffer (0.1 M sodium acetate, 1 M sodium chloride, 1 mM calcium chloride and 0.01% sodium azide) from the gel. Incubations were performed in test tubes containing 100 $\mu$l gel suspension (Con A Sepharose or Sepharose respectively), binding buffer and various amounts of dextran ferrofluid and glucose. The total volume of the suspension was 1 ml. After over-night incubation the tubes were centrifuged at 3500 g for 5 minutes and the supernatant was removed and measured for turbidity. The gel was washed with binding buffer and quantitatively removed into a measuring vessel, which was made of glass (5 mm diameter×10 cm) and specially designed to be inserted into the measuring coil.

Turbidity measurements

After incubation with Con A Sepharose or Sepharose (in the direct or the competitive detection mode), the dextran ferrofluid content in the supernatant was measured. This was performed using an Ultraspec III spectrophotometer from Pharmacia LKB (Sweden), at a wavelength of 400 nm. The amount of bound dextran ferrofluid was calculated by recording the difference in the turbidity of the supernatant before and after incubation, and assuming that this concentration difference had accumulated in the gel phase. A linear relationship was seen between the turbidity (at 450 nm) and the dextran ferrofluid concentration (0–150 $\mu$g Fe/mL).

Magnetic permeability measurements The transducer used in this work measures changes in the magnetic permeability of materials and constitutes a coil $L_4$ which is a part of a balanced Maxwell bridge, with two variable resistances, $R_1$ and $R_3$. The bridge is balanced if the following equations are fulfilled: $L_4=R_2R_3C_1$ and $R_4=R_2R_3/R_1$. Other circuits, including, for example, unbalanced bridges and circuits with multiple coils, are also contemplated in the present invention, as will be appreciated by those of ordinary skill in the art.

Figure 4:
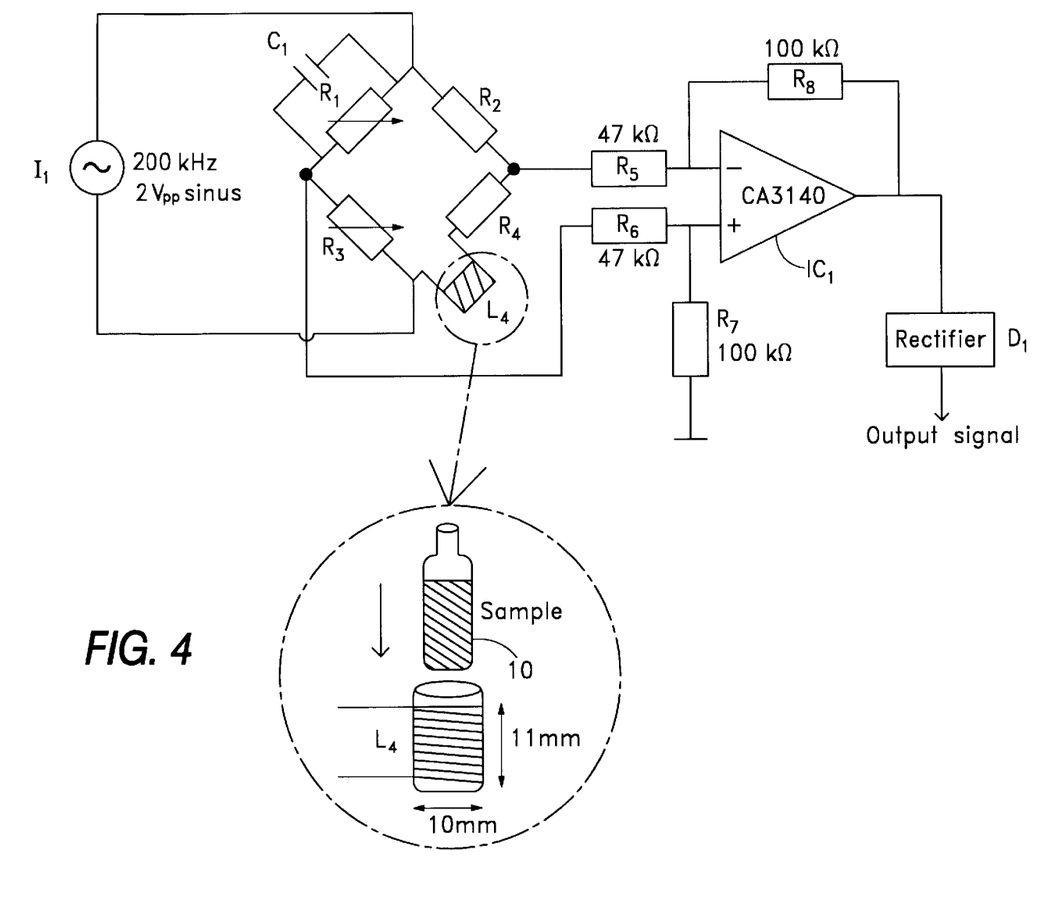
FIG. 4 is a schematic representation of a Maxwell bridge assembly including a coil for transducing a magnetic permeability signal in a sample.

As shown in FIG. 4, which is a diagram of the transducer assembly, the measuring coil $L_4$ (transducer) has a length of 11 mm, a radius of 10 mm, and 30 turns of closely packed wire and is part of a balanced Maxwell bridge. The other components in the Maxwell bridge are $R_1$=2860 $\Omega$ (10 k $\Omega$ potentiometer), $C_1$=1 nF, $R_2$=180 $\Omega$, $R_3$=27 $\Omega$ (100 $\Omega$ trimpotentiometer), $R_4$=0.44 $\Omega$, and $L_4$=4.9 $\mu$H. A sinusoidal wave of frequency 200 kHz and amplitude 2V peak-to-peak is fed into the bridge from a voltage source $I_1$. A sample 10 is inserted into the coil $L_4$, which causes a deflection current in the coil as a function of the magnetic permeability. The voltage difference, comparing the voltage before the sample 10 is inserted with the voltage after the sample 10 is inserted, is further processed by a differential operational amplified circuit. This circuit includes $R_5$ and $R_6$, both 47 k $\Omega$, $R_7$ and $R_8$, both 100 k $\Omega$ and $IC_1$ 3140, which is a commercially available operational amplifier. The signal is rectified at $D_1$ and is finally recorded by a chart writer. The introduction of ferromagnetic materials inside the coil causes an increase in the voltage difference over the Maxwell bridge. This, in turn, indicates that binding took place. In a similar manner, an almost unlimited number of analytes can be detected using any of the well-known binding interactions between such analytes and specific binding molecules. Such molecules include antibodies, lectins, enzyme-substrate, receptor-target, and the like, as well as covalent binding by any conventional reaction.

Figure 5:
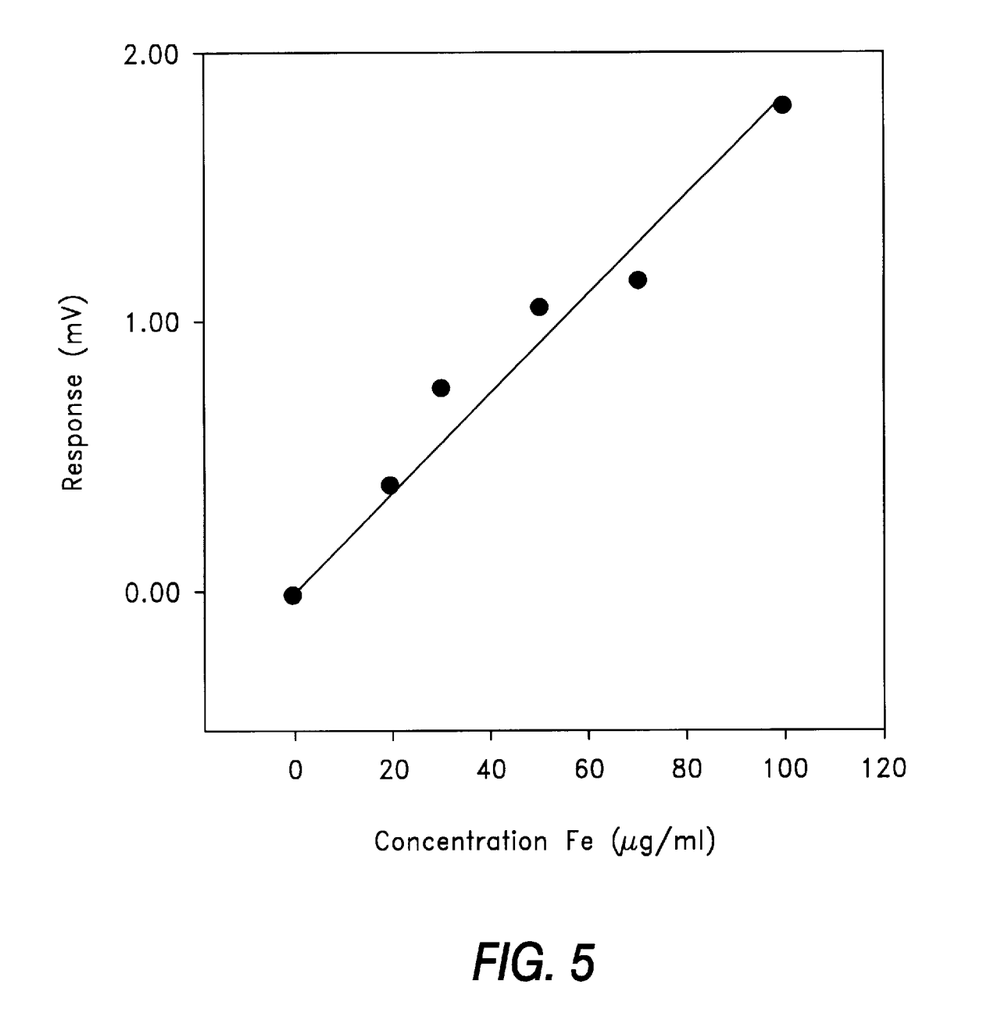
FIG. 5 shows the linear relationship between Maxwell bridge measurements and the concentration of iron oxide-dextran particles in a measuring solution.

Example 2. Identification of a Usable Marker for Magnetic Permeability Measurements To identify a usable marker we tested iron oxide-dextran particles, which have a high magnetic permeability. Because of the size of these particles (presumably 1–300 nm), a solution containing them would be colloidal. The dextran shell helps prevent aggregation of the particles. Measurements of the magnetic permeability on solutions containing different concentrations of such particles were taken. The solutions were placed in a measuring coil and inductance changes noted. The inductance change in turn affected either the resonance frequency for an LC-circuit in which the coil was a part, or the balancing (see FIG. 5), expressed as a difference in voltage or response, in a Maxwell bridge in which the coil was a part.

The relationship between the change of resonance frequency in Hz, or the voltage difference (response) in mV, is in a linear relationship against the number of particles in the measuring solution, expressed as iron concentration. This example illustrates that it is possible to use the described techniques, based on measurements on the magnetic permeability, to determine the amount of marker/analyte in, for example, a solution, gel, or suspension. This is particularly useful where determinations of the decrease in the amount of maker/analyte in measurement solution is to be determined.

Example 3. Chemical Analysis of a Model Ferromagnetic Analyte

Figure 2:
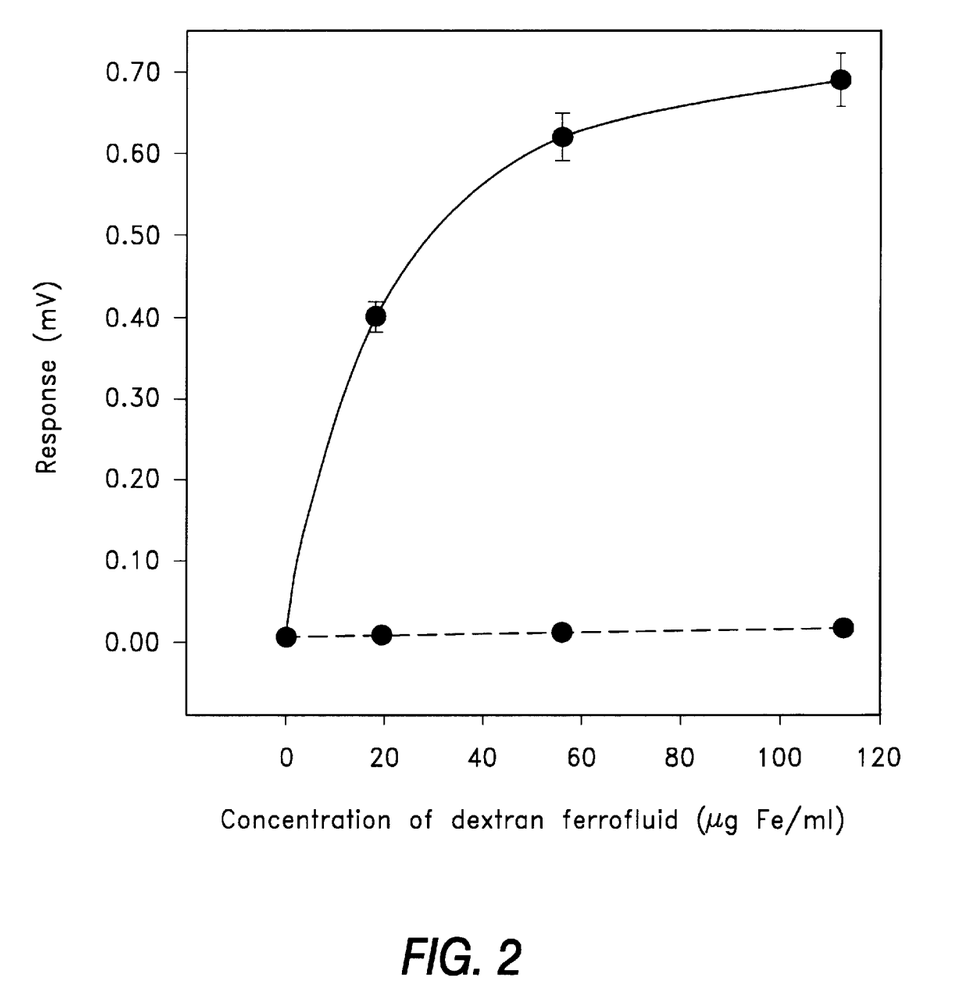
FIG. 2 provides Maxwell bridge measurements of Concanavalin A-sepharose that has been incubated in measuring solutions containing different amounts of iron oxide-dextran particles as a model analyte.

Iron oxide-dextran particles were tested as a model ferromagnetic analyte, representing any other analytes which have sufficient magnetic permeability to make a chemical analysis possible, even without extraneous markers. Con A, which binds to dextran and other carbohydrates, was chosen as the recognition element. For this Example, Con A was immobilized to a Sepharose gel carrier. After incubation in the measuring solutions containing different concentrations of the model analyte, the Maxwell bridge as described earlier, was used for the analysis of the magnetic permeability of the formed complex. FIG. 2 shows that voltage difference increases with the initial amount of model analyte in the measuring solution (expressed in concentration of iron). When the same experiment was done with a Sepharose gel carrier that was lacking Con A, no voltage change was observed (lower curve). This result confirms the importance of the molecular recognition for the chemical analysis.

These experiments served as a demonstration of a direct detection of ferromagnetic substances using a magnetic transducer in combination with a biorecognition element, such as might be applied in a bioassay—biosensor. In this particular case, ferromagnetic dextran ferrofluid and Con A Sepharose were used. However, ferrofluids are commercially available for biomagnetic separations in immuno-, molecular-, cell-diagnostics and therapeutics. Such materials can be easily analyzed qualitatively and quantitatively, using the described direct detection approach.

The direct detection approach has, due to the small amount of ferromagnetic substances of interest, less potential compared to the sequential binding and the competitive detection modes. With sequential binding or competition, almost any analyte, from small metabolites to nucleic acids, enzymes, proteins, viruses and cells, can be detected.

Example 4. Competition Analysis Measuring a Non-ferromagnetic Analyte

Chemical analysis was next performed using an analyte, glucose, which has a low magnetic permeability ($\mu_r \approx 1$). This analysis was based on competition between the analyte and a ferromagnetic marker. With a competition analysis, it is possible to quantitatively and qualitatively measure the amount of a non-ferromagnetic analyte. The competition assay used glucose as a model analyte, with iron oxide-dextran particles (described above) being used as the competitive marker, and Con A as the recognition element. Con A was immobilized to a carrier, Sepharose gel. Because glucose and the marker (by its dextran component) both have affinity for Con A, they competed with each other for binding to Con A. In samples having no glucose, or low concentrations of glucose, only the ferromagnetic marker bound to the recognition element. With increased amounts of glucose in the reaction, the marker represented a progressively smaller proportion of the total bound material. By this method it is possible to determine the amount of glucose in an unknown sample. By placing the recognition element, Con A, inside the coil, the amount of bound marker can be determined for different glucose concentrations.

Figure 3:
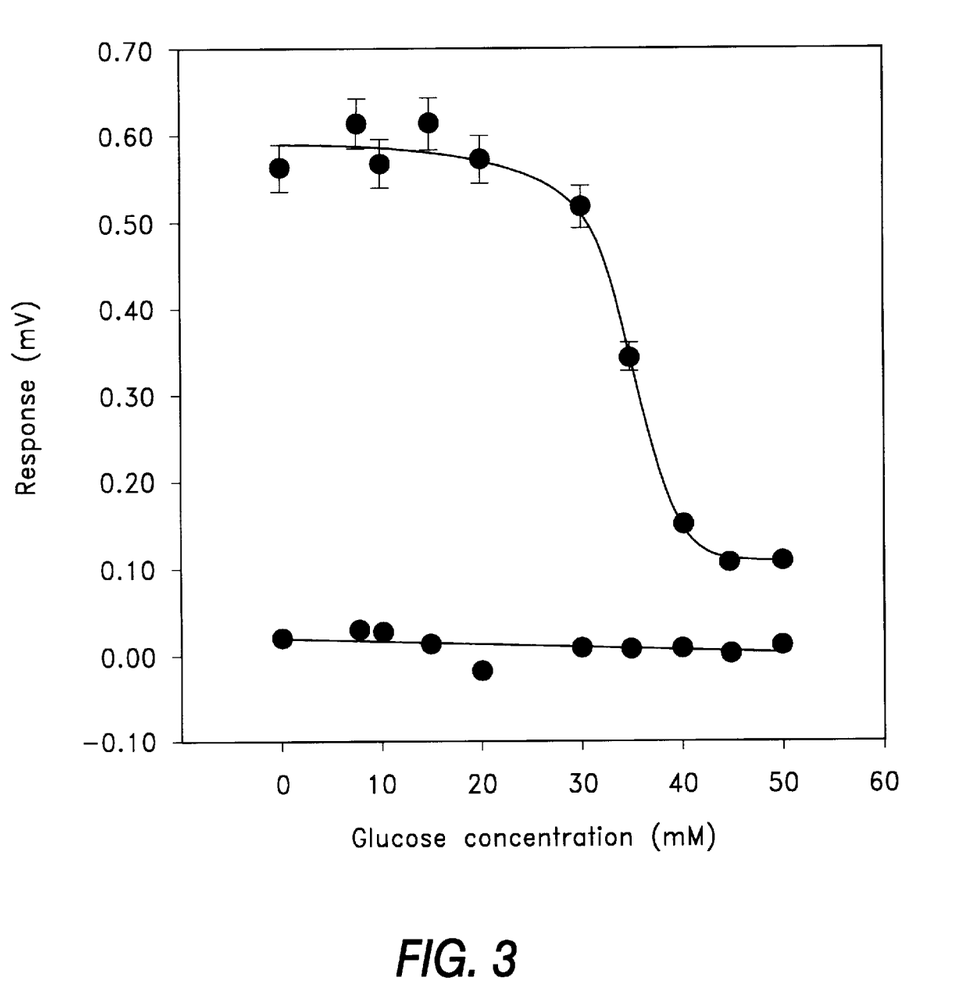
FIG. 3 compares Maxwell bridge measurements of Concanavalin A-sepharose which has been incubated in measuring solutions containing different amounts of glucose, as the model analyte, and a constant amount of iron oxide-dextran particles, which function both as marker and competitive analogue to the model analyte.

The result of this procedure is shown in FIG. 3. This calibration curve shows that the voltage difference of the Maxwell bridge, after adjusting for maximal binding of the marker, is related to the glucose concentration in the measuring solution (upper curve). The control experiment, without Con A as a recognition element, confirms that the absence of molecular recognition gives no change in the magnetic permeability of the sample (lower curve). We have also performed this measurement on glucose with the recognition element immobilized inside the coil, which demonstrated a chemical (bio)sensor for glucose.

The competition curve shown in FIG. 3 has a very sharp response decrease in the concentration range 20–40 mM. This dynamic range could potentially be used for the determination of glucose. By changing the binding conditions (such as pH or ion strength) or initial concentration of dextran ferrofluid the concentration interval for the dynamic range could be altered. In competitive assays in general, the difference in affinity constants for the analyte and competitor determine the detection interval of the analyte.

Example 5. Characterization of the Magnetic Transducer

Figure 6:
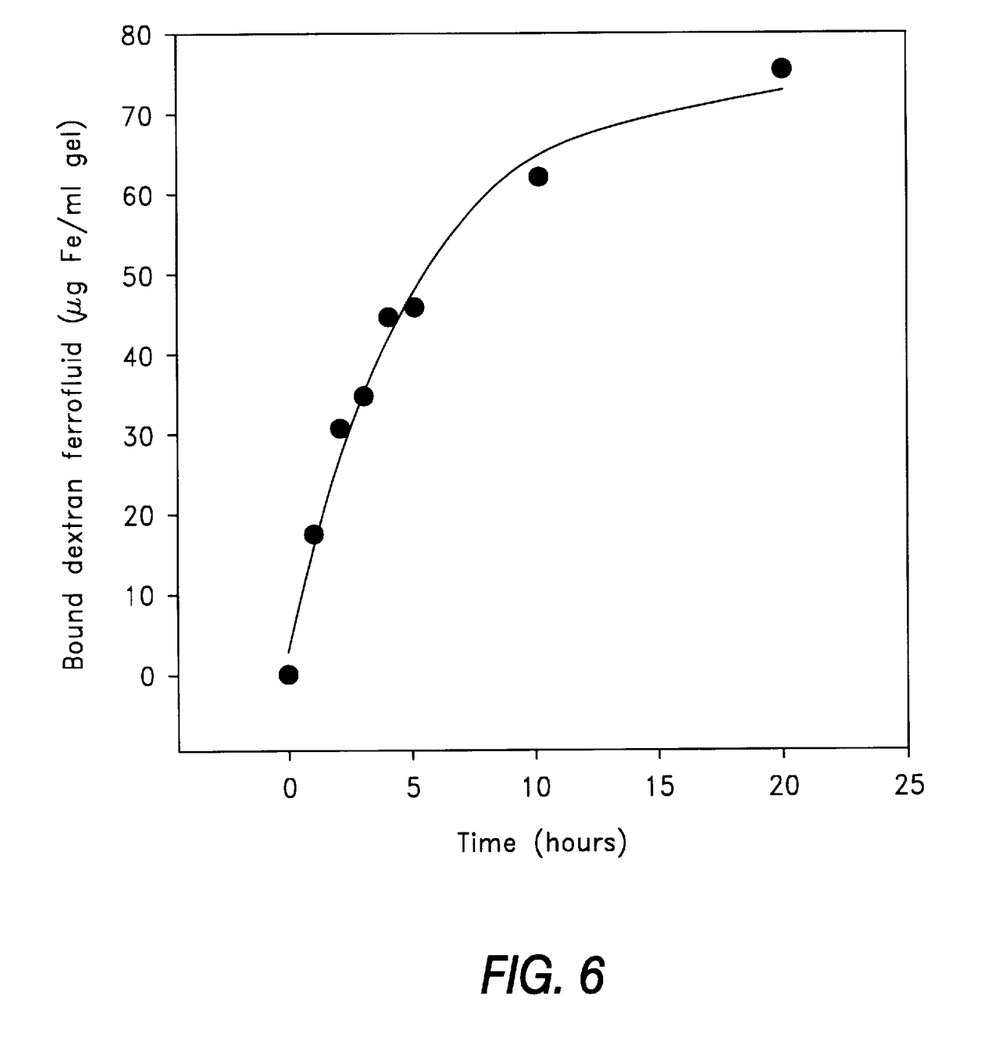
FIG. 6 is a curve showing the kinetics of binding of dextran ferrofluid to Con A sepharose beads.

There are several different approaches which may be utilized for the determination of the inductance of a coil. These include, for instance, resonance frequency measurements of a parallel circuit containing the coil and a capacitor, various bridge measurements, transient measurements, inductive coupling between two coils, and impedance measurements. We initially attempted resonance frequency measurements, but this method gave poor results. The sensitivity observed was about 100–1000 times less than that using the Maxwell bridge approach. The output signal from the Maxwell bridge was proportional to the concentration of ferromagnetic dextran ferrofluid solution (expressed in µg Fe/ml) that was placed within the measuring coil. The sensitivity was 18 µV/(µg Fe/ml). The detection limit was thus 2 pM dextran ferrofluid particles (calculation based on 100 nm sized ferrofluid particles). See FIG. 6.

A commercially available dextran ferrofluid (D-8517, SIGMA) was also tested. However, this was not ferromagnetic because it contained the iron in the form of iron hydroxide, $Fe(OH)_3$ and not as magnetite, $Fe_3O_4$. Consequently, no response was observed when this dextran ferrofluid was placed within the measuring coil.

Example 6. Detection of Macromolecules

The sensitivity of detection available with the present invention allows the identification and quantification of non-abundant macromolecules. A blood sample is taken from a patient, and the erythrocytes are removed by centrifugation. The supernatant is then contacted with beads crosslinked to an unlabeled monoclonal antibody that is specific to a viral coat protein. Picomolar quantities of the coat protein are present in the blood sample, and the protein becomes bound to the beads due to the protein's affinity for the antibody. The beads are washed to remove non-specifically bound macromolecules.

A second preparation of the antibody is labeled with a ferromagnetic material, but is not crosslinked to beads. This soluble antibody marker is then contacted with the washed beads, and a sequential binding complex is formed, with the bead-immobilized coat protein being bound by the labeled antibody. The sample tube is passed within a coil that is part of a Maxwell bridge. The small quantities of ferromagnetic label immobilized by the sequential binding reaction induce a change in the magnetic permeability of the sample. The change indicates presence of the coat protein, and an aggressive treatment protocol is begun to slow the progress of the viral infection.

Example 7. Detection of Tumor Cells in Tissue

A small amount of soluble antibody ferromagnetic marker is injected into a patient. After an incubation period the marker is accumulated in tissues containing tumor cells against which the antibodies are directed. A small tissue sample is taken as a biopsy from the suspected area and put directly into the coil of the present invention. No sample pre-treatment is necessary prior to measurement. Detection of an increased magnetic permeability of the tissue sample indicates malignancy.

In a close variant of this approach, a biopsy is taken from a patient without first treating the patient with a ferromagnetic marker antibody. Instead, the biopsy tissue is exposed to the antibody marker in vitro. After incubation with the antibody, the tissue is washed and its magnetic permeability is measured. An elevated magnetic permeability indicates malignancy.

In another variant of this approach, a limiting amount of tumor-specific ferromagnetic marker antibody is added to biopsy tissue and incubated therewith in vitro. Simultaneously, a second sample of the same antibody, in the same quantity, is incubated with a equal amount of control tissue known not to include malignant cells. Afterward, the biopsy tissue is removed from the incubation medium by centrifugation, and the supernatant is placed into the coil, where its magnetic permeability is compared to that of the control sample similarly treated. A lower magnetic permeability for the biopsy sample supernatant, relative to the control, indicates the depletion of the ferromagnetic marker antibody by the biopsy tissue, thus implying that the biopsy tissue is malignant.

Example 8. Magneto Immuno Assay Using a Carrier

A blood sample is taken from a patient and put in a tube pre-loaded with carrier beads that are crosslinked to an unlabeled monoclonal antibody, specific for epitope 1. The tube also contains a soluble monoclonal ferromagnetic marker antibody that is specific for epitope 2. In the presence of the cancer indicator alpha pheto protein (AFP), for which the monoclonal antibodies are selected, an aggregation occurs between the crosslinked beads, the AFP, and the ferromagnetic marker antibody. The aggregates are concentrated at the bottom of the test tube by being allowed to sediment or by centrifugation. Technician safety is enhanced by the fact that at no point in the aggregation/sedimentation process is it necessary to reopen the tube for washing, reagent addition, or like steps.

With the aggregates sufficiently sedimented, the bottom part of the tube is placed into the coil. The presence of AFP in the sample causes a high magnetic permeability in the sample and indicates malignancy in the patient. The detection limit of this method is in the picomolar range as the binding ratio between the analyte, AFP, and the antibody marker is at least 1:1. An even more sensitive level of detection can be obtained if a polyclonal antibody marker is used, due to the higher binding ratio.

What is claimed is:

1. A system for in vitro detection of an analyte, said system comprising a marker, a recognition element, and a transducer, and a vessel, said marker comprising a material having an externally, inductively detectable relative magnetic permeability constant of at least about 600, said recognition element being capable of binding to or competing for binding with said analyte in said vessel, and said transducer being adapted to be induced proportional to a magnetic permeability of a sample, wherein said transducer comprises a coil, and wherein said vessel containing said sample is introduced into said coil, wherein said marker and said recognition element act to induce in said transducer a first inductance value when said analyte is absent from said sample, and a second inductance value when said analyte is present in said sample.

2. The system of claim 1, wherein said marker specifically binds to said analyte.

3. The system of claim 1, wherein said marker competes with said analyte for binding to said recognition element.

4. The system of claim 1, wherein said recognition element is linked to said marker.

5. The system of claim 1, wherein said recognition element and said marker both bind to said analyte.

6. The system of claim 1, wherein said analyte comprises said marker.

7. The system of claim 1, wherein said analyte comprises a protein.

8. The system of claim 1, wherein said analyte comprises a nucleic acid.

9. The system of claim 1, wherein said analyte comprises a hormone.

10. The system of claim 1, wherein said analyte comprises an antibody.

11. The system of claim 1, wherein said analyte comprises a virus.

12. The system of claim 1, wherein said analyte comprises a cell.

13. The system of claim 1, wherein said second inductance value is quantitatively proportional to a concentration of said analyte in said sample.

14. The system of claim 1, wherein said sample comprises a soluble solution or a suspension.

15. The system of claim 14, wherein said sample comprises a centrifugation supernatant.

16. The system of claim 1, wherein said sample comprises a particulate fraction.

17. The system of claim 16, wherein said sample comprises a centrifugation pellet.

18. The system of claim 16, wherein said sample comprises cells.

19. The system of claim 16, wherein said sample comprises viruses.

20. The system of claim 16, wherein said sample comprises beads.

21. The system of claim 1, wherein said material comprises an element selected from the group consisting of iron, nickel, cobalt, gadolinium and manganese.

22. The system of claim 21, wherein said material is an alloy.

23. The system of claim 21, wherein said material is a semiconductor.

24. The system of claim 21, wherein said material is a chemical compound.

25. The system of claim 1, wherein said transducer comprises a coil adapted to accept inductance proportional to said magnetic permeability of said sample.

26. The system of claim 1, wherein said transducer comprises an electronic measuring bridge.

27. The system of claim 26, wherein said electronic measuring bridge comprises a Maxwell bridge.

28. The system of claim 1, wherein said transducer comprises an LC-circuit.

29. A method of detecting an analyte, comprising the steps of:

providing a sample, said sample comprising a marker and a recognition element, said marker comprising a material having an externally, inductively detectable relative magnetic permeability constant of at least about 600, said recognition element being capable of binding to or competing for binding with said analyte, said marker and said recognition element being adapted to cooperate to induce in a transducer comprising a coil a first inductance value when said analyte is absent from said sample, and a second inductance value when said analyte is present in said sample;

inducing an inductance value in said transducer by positioning said sample in said coil of said transducer in vitro; and determining whether said analyte is absent or present in said sample, based on said inductance value induced in said inducing step.

30. The method of claim 29, wherein said marker specifically binds to said analyte.

31. The method of claim 29, wherein said marker competes with said analyte for binding to said recognition element.

32. The method of claim 29, wherein said recognition element is linked to said marker.

33. The method of claim 29, wherein said recognition element and said marker both bind to said analyte.

34. The method of claim 29, wherein said analyte comprises said marker.

35. The method of claim 29, wherein said analyte comprises a protein.

36. The method of claim 29, wherein said analyte comprises a nucleic acid.

37. The method of claim 29, wherein said analyte comprises a hormone.

38. The method of claim 29, wherein said analyte comprises an antibody.

39. The method of claim 29, wherein said analyte comprises a virus.

40. The method of claim 29, wherein said analyte comprises a cell.

41. The method of claim 29, wherein said second inductance value is quantitatively proportional to a concentration of said analyte in said sample.

42. The method of claim 29, wherein said sample comprises a soluble solution or a suspension.

43. The method of claim 42, wherein said sample comprises a centrifugation supernatant.

44. The method of claim 29, wherein said sample comprises a particulate fraction.

45. The method of claim 44, wherein said sample comprises a centrifugation pellet.

46. The method of claim 44, wherein said sample comprises cells.

47. The method of claim 44, wherein said sample comprises viruses.

48. The method of claim 44, wherein said sample comprises beads.

49. The method of claim 29, wherein said material comprises an element selected from the group consisting of iron, nickel, cobalt, gadolinium and manganese.

50. The method of claim 49, wherein said material is an alloy.

51. The method of claim 49, wherein said material is a semiconductor.

52. The method of claim 49, wherein said material is a chemical compound.

53. The method of claim 29, wherein said transducer comprises a coil adapted to accept inductance proportional to said magnetic permeability of said sample.

54. The method of claim 29, wherein said transducer comprises an electronic measuring bridge.

55. The method of claim 54, wherein said electronic measuring bridge comprises a Maxwell bridge.

56. The method of claim 29, wherein said transducer comprises an LC-circuit.

57. The method of claim 29, wherein said positioning comprises flowing said sample through said vicinity of said transducer.

58. A method for detecting the presence of an analyte, comprising the steps of:

contacting, in vitro, a sample suspected of containing said analyte with a reagent that binds to or competes for binding with or by said analyte, said reagent including a component having an externally, inductively detectable relative magnetic permeability constant of at least about 600;

separating unbound reagent from bound reagent; and detecting or measuring the bound or unbound reagent as an indication of the presence, absence, or quantity of said analyte in said sample by placing said sample in a coil of a transducer adapted to be induced proportional to a magnetic permeability of said sample.

* * * * *